US010016453B2

(12) United States Patent
Imran

(10) Patent No.: US 10,016,453 B2
(45) Date of Patent: Jul. 10, 2018

(54) IN VITRO BIO-REACTOR CIRCUIT

(71) Applicant: INCUBE LABS, LLC, San Jose, CA (US)

(72) Inventor: Mir Imran, Los Altos Hills, CA (US)

(73) Assignee: INCUBE LABS, LLC, San Jose, CA (US)

( * ) Notice: Subject to any disclaimer, the term of this patent is extended or adjusted under 35 U.S.C. 154(b) by 0 days.

(21) Appl. No.: 15/709,373

(22) Filed: Sep. 19, 2017

(65) Prior Publication Data
US 2018/0140629 A1 May 24, 2018

Related U.S. Application Data

(63) Continuation of application No. 12/316,809, filed on Dec. 12, 2008, now Pat. No. 9,763,977, which is a continuation-in-part of application No. 10/664,697, filed on Sep. 16, 2003, now abandoned.

(51) Int. Cl.
C07K 14/00 (2006.01)
A61K 31/785 (2006.01)
C07K 14/78 (2006.01)
A61L 27/22 (2006.01)

(52) U.S. Cl.
CPC .......... *A61K 31/785* (2013.01); *A61L 27/227* (2013.01); *C07K 14/001* (2013.01); *C07K 14/78* (2013.01)

(58) Field of Classification Search
None
See application file for complete search history.

(56) References Cited

U.S. PATENT DOCUMENTS

| 4,318,905 | A | 3/1982 | Nestor et al. |
| 5,229,490 | A | 7/1993 | Tam |
| 5,354,736 | A | 10/1994 | Bhatnagar |
| 5,827,729 | A | 10/1998 | Naughton et al. |
| 5,882,645 | A | 3/1999 | Toth et al. |
| 5,958,428 | A | 9/1999 | Bhatnagar |
| 5,981,211 | A | 11/1999 | Hu et al. |
| 5,998,202 | A * | 12/1999 | Schwarz ............... C12M 23/00 435/297.1 |
| 6,159,531 | A | 12/2000 | Dang et al. |
| 6,268,348 | B1 | 7/2001 | Bhatnagar |
| 6,580,563 | B1 | 6/2003 | Finney |
| 6,635,482 | B1 | 10/2003 | Yu et al. |
| 6,942,799 | B2 | 9/2005 | Corcho-Sanchez et al. |
| 9,763,977 | B2 | 9/2017 | Imran |
| 2002/0062145 | A1 | 5/2002 | Rudakov et al. |
| 2003/0113478 | A1 | 6/2003 | Dang et al. |
| 2004/0072746 | A1 | 4/2004 | Sullivan et al. |
| 2005/0063937 | A1 | 3/2005 | Li et al. |
| 2006/0166354 | A1 | 7/2006 | Wikswo et al. |
| 2012/0201858 | A1 | 8/2012 | Li et al. |

FOREIGN PATENT DOCUMENTS

| WO | WO 91/002537 A1 | 3/1991 |
| WO | WO 02/068588 A2 | 9/2002 |
| WO | WO 05/027957 A1 | 3/2005 |
| WO | WO 10/068280 A1 | 6/2010 |

OTHER PUBLICATIONS

Bhatnagar et al., "Construction of Bliomimetic Environments with a Synthetic Peptide Analogue of Collagen," Materials Research Society, Symposium Proceedings, 530:4.3-54, (1998).
Bhatnagar et al., "Design of Biomirnetic Habitats for Tissue Engineering with P-15, a Synthetic Peptide Analogue of Collagen," Tissue Engineering, 5(1):53-65 (1999).
Bhatnagar et al., "The Role in Cell Binding of a α-bend within the Triple Helical Region in Collagen α1 (I) Chain: Structural and Biological Evidence for Conformational Tautomerisrn on Fiber Surface," Journal of Biomolecular Structure & Dynamics, 14(5):547-560, (1997).
Davis et al., "Immobilization of RGD to <111> silicon surfaces for enhanced cell adhesion and proliferation " Biomaterials, 23:4019-4027 (2002).
Dickeson et al., "Ligand recognition by the I domain-containing Integrins," Cell. Mol. Life Sci., 54:556-566 (1998).
Gumpenberger et al., "Adhesion and proliferation of human endothelial cells on photo-chemically modified polytetrafluoroethylene," Biomaterials, 24(28):5139-44, (2003).
Haigh et al., "Synthesis and properties of amphiphilic networks 2: a differential scanning calorimetric study of poly(dodecyl methacrylete-stet-2.3 propanclid-1-methacrylete-sfetethandid diomethacrytete) networks and adhesion and spreading of dermal fibroblasts on these materials," Biomaterials, 23:3509-3516, (2002).
Janssen et al., "Coating with genetic engineering hydrophobin promotes growth of fibroblasts on a hydrophobic solid," Biomaterials, 23:4847-4854, (2002).
Koo et al., "Co-regulation of cell adhesion by nanoscale RGD organization and mechanical stimulus," Journal of Cell Science, 115:1423-1433 (2002).
Middleton et al., "Synthetic biodegradable polymers as orthopedic devices," Biomaterials, 1:2335-2346 (2000).
Nomizu et al., "Multimeric forms of the active laminin peptide YIGSR enhance the inhibition tumor growth and metastasis," Peptide Chemistry, pp. 249-252 (1993).
Pakalns et al., "Cellular recognition of synthetic peptide amphiphiles in self-assembled monolayer films," Biomaterials, 20:2265-2279, (1999).
Posnett et al., "A novel method for producing anti-peptide antibodies," The Journal of Biological Chemistry, 263(4):1719-1725, (1998).

(Continued)

Primary Examiner — Jeanette M Lieb
(74) Attorney, Agent, or Firm — Alston & Bird LLP

(57) ABSTRACT

Embodiments of the invention provide bio-reactor circuits for in vitro research applications. One embodiment provides a bio-reactor circuit comprising at least one bio-reactor and a pump fluidically coupled to the at-least-one bio-reactor. The bio-reactor comprises a housing having inlet and outlet ports and first and second chambers. The chambers are separated by a porous membrane with the first chamber providing a flow path for a fluid. The membrane includes a coating having a cell binding affinity for the attachment and proliferation of cells to cover the surface of the membrane. The second chamber provides a volume for maintaining the viability of cells disposed in the chamber. The cells can be selected to produce a biochemical compound. The membrane is configured to allow for diffusion of the compound from the second chamber into the flow path as well as allow for diffusion of gases, nutrients and other biochemical compounds.

22 Claims, 19 Drawing Sheets

(56) References Cited

OTHER PUBLICATIONS

Qian et al., "Enhanced cell attachment to anorganic bone mineral in the presence of a synthetic peptide related to collagen," Journal of Biomedical Materials Research, 31:545-554, (1996).
Shin et al., "Eflomimetic materials for tissue engineering," Biomaterials, 24:4353-4364, (2003).
Sieminski et al., "Tiomaterial—microvasculature interactions," Biomaterials, 21:2233-2241, (2000).
Tam et al., "Synthesis and Applications of Branched Peptides in Immunological Methods and Vaccines," Peptides: Synthesis, Structures, and Applications, B. Gutte (ed), Academic Press, pp. 455-500, (1995).
Wong et al., "Identification and validation of a novel cell-recognition site (KNEED) on the $8^{o1}$ type III domain of fibronectin," Biomaterials, 23:3865-3870, (2002).
Yuehuei et al., "Pre-clinical in vivo evaluation of orthopaedic bioabsorbable devices," Biomaterials, 21:2635-2652, (2000).
U.S. Appl. No. 10/664,697, Examiners Answer to Appeal Brief mailed Apr. 1, 2010.
U.S. Appl. No. 10/664,697, Final Rejection dated Apr. 19, 2007.
U.S. Appl. No. 10/664,697, Final Rejection dated Dec. 23, 2008.
U.S. Appl. No. 10/664,697, Non-Final Rejection dated Jan. 9, 2008.
U.S. Appl. No. 10/664,697, Non-Final Rejection dated Jul. 27, 2006.
U.S. Appl. No. 10/664,697, Patent Board Decision mailed Jun. 22, 2011.
U.S. Appl. No. 10/664,697, Restriction Requirement dated Mar. 22, 2006.
U.S. Appl. No. 12/316,809, Final Rejection dated Mar. 29, 2013.
U.S. Appl. No. 12/316,809, Non Final Rejection dated Apr. 27, 2012.
U.S. Appl. No. 12/316,809, Non-Final Office Action dated Nov. 30, 2016.
U.S. Appl. No. 12/316,809, Notice of Allowance dated May 18, 2017.
U.S. Appl. No. 12/316,809, Restriction Requirement dated Dec. 6, 2011.
U.S. Appl. No. 13/136,885, Non-Final Office Action dated Apr. 17, 2014.
U.S. Appl. No. 13/136,885, Requirement for Restriction/Election dated Sep. 5, 2013.
WIPO Application No. PCT/US2004/029951, International Preliminary Examination Report completed Jun. 13, 2005.
WIPO Application No. PCT/US2004/029951, PCT International Search Report dated Jun. 31, 2005.
WIPO Application No. PCT/US2004/029951, Written Opinion of the International Searching Authority dated Jan. 31, 2005.
WIPO Application No. PCT/US2009/006504, PCT International Preliminary Report on Patentability dated Jun. 14, 2011.
WIPO Application No. PCT/US2009/006504, PCT International Search Report dated Feb. 23, 2010.
WIPO Application No. PCT/US2009/006504, PCT Written Opinion of the International Searching Authority dated Feb. 23, 2010.

* cited by examiner

SEQUENCE LISTING

```
<160> NUMBER OF SEQ ID NOS: 13

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Gly Thr Pro Gly Pro Gln Gly Ile Ala Gly Gln Arg Gly Val Val
1               5                   10                  15

<210> SEQ ID NO 2
<211> LENGTH: 3
<212> TYPE: PRT
<213> ORGANISM: Artificial Sequence
<220> FEATURE:
<223> OTHER INFORMATION: Synthetic peptide
```

<400> SEQUENCE: 2

Arg Gly Asp
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Arg Glu Asp Val
1

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Trp Gln Pro Pro Arg Ala Arg Ile
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Tyr Ile Gly Ser Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Ser Ile Lys Val Ala Val
1               5

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

Arg Tyr Val Val Leu Pro Arg Pro Val Cys Phe Glu Lys Gly Met Asn
1               5                   10                  15

Tyr Thr Val Arg
            20

<210> SEQ ID NO 8
<211> LENGTH: 13
<212> TYPE: PRT
<213> ORGANISM: Artificial Sequence

```
<220> FEATURE:
<223> OTHER INFORMATION: Synthetic peptide

<400> SEQUENCE: 8

Gly Glu Phe Tyr Phe Asp Leu Arg Leu Lys Gly Asp Lys
1               5                   10

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide

<400> SEQUENCE: 9

Gly Ile Ala Gly
1

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Gln Gly Ile Ala Gly Gln
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide

<400> SEQUENCE: 11

Lys Asn Glu Glu Asp
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Pro Asp Ser Gly Arg
1               5

<210> SEQ ID NO 13
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (17)
<223> OTHER INFORMATION: Beta Ala

<400> SEQUENCE: 13

Gly Thr Pro Gly Pro Gln Gly Ile Ala Gly Gln Arg Gly Val Val Lys
1               5                   10                  15

Ala
```

IN VITRO BIO-REACTOR CIRCUIT

CROSS-REFERENCES TO RELATED APPLICATIONS

This application is a continuation of U.S. patent application Ser. No. 12/316,809 filed Dec. 12, 2008, which is a continuation in part of U.S. patent application Ser. No. 10/664,697 filed Sep. 16, 2003 which is incorporated by reference herein in its entirety.

REFERENCE TO A SEQUENCE LISTING

This application includes an electronic sequence listing in a file named 504482SEQLST.TXT, created on Feb. 1, 2018, and containing 2,513 bytes, which is hereby incorporated by reference in its entirety for all purposes.

BACKGROUND OF THE INVENTION

Field of the Invention

Embodiments of the invention relate to apparatus, systems and methods for an in vitro bio reactor circuit. More specifically, embodiments of the invention relate to apparatus and systems and methods for using a bio-reactor circuit to study organ systems in vitro.

While there have been many advancements in the treatment of various diseases using drug, cellular and related therapies one of the limiting factors is the unpredictability in moving in vitro bench testing of a new drug or related therapy to an in vivo setting whether in an animal model or human subjects. This is due to the inability to know how the drug or other therapy will affect the target organ as well as other non-target organs both in terms of efficacy and toxicity. Often a drug can have toxic or other detrimental effects on non-target organs systems or even the target organ which cannot be ascertained until the drug is tested in vivo in an animal model. Even drugs that pass animal testing can fail human trials due to differences between animal and human cell types, organ systems and pharmacokinetics (e.g., clearance by the kidney). By the time a drug reaches human trials, tens of millions of dollars or more may have been spent on research and development. Even getting a drug to animal testing can be costly. Failure at any of these stages, particularly at the point of human trials, is very cost prohibitive. Thus, there is a need for apparatus and systems for simulating in vivo conditions under an in vitro setting so as to streamline the drug screening and overall drug development process.

SUMMARY OF THE INVENTION

Various embodiments of the invention provide an in vitro bio reactor circuit useful for studying one or more organ systems on an in vitro basis. Particular embodiments can be used to study the effects of pharmaceuticals and other treatments on multiple organ systems at the same time. In many embodiments, the circuit includes one or more bio-reactors that are coupled to a nutrient solution reservoir and a pump.

One embodiment of the bio-reactor circuit comprises at least one bio-reactor and a pump fluidically coupled to the least one bio-reactor. The at least one bio-reactor comprises a housing having an inlet and outlet port, a first chamber and a second chamber. The chambers are separated by a porous membrane with the first chamber providing a flow path for a nutrient or other solution flowing through the bio-reactor. The membrane includes a coating having a cell binding affinity configured for the attachment and proliferation of sufficient endothelial or other cells to cover the surface of the membrane (typically the surface exposed to the first chamber). The second chamber provides a volume for maintaining the viability of a plurality of cells disposed in the chamber such as hepatic, pancreatic, renal or bone marrow cells. The cells can be selected or otherwise conditioned to produce a biochemical compound such as insulin. The membrane is arranged and configured to allow for the diffusion of the compound from the second chamber into the flow path as well as allow for the diffusion of gases, nutrients and other biochemical compounds (e.g., drugs, hormones and like compounds) into and out of the second chamber. In particular embodiments, the second chamber can comprise a plurality of tubular membrane structures with one cell line in their interior and an external coating promoting the deposition of endothelial, smooth muscle or other cells on their exterior. In one embodiment, the tubular structure can comprise PTFE with a multi arm peptide coating.

The pump can be continuous or pulsatile so as to simulate arterial venous or other circulation. The membrane can be fabricated from various porous materials and is desirably sufficiently porous and/or permeable to allow for the diffusion of nutrients from the surface of the membrane into the interior of the second chamber so as to maintain the viability of the cells as well as allow the outward diffusion of gases and compounds secreted by the cells. The surface of the membrane can have a convoluted or other shape to enhance diffusion. The membrane surface can also include a protein or other coating or layer that facilitates cell attachment and growth of cells such as endothelial or smooth muscle cells (typically, the surface exposed to the first chamber, the other surface can also be coated). An attached cell layer can be achieved by circulating a solution containing endothelial or other cells through the bio-reactor under conditions suitable for the cells to attach and grow. The plurality of cells disposed within the second chamber can be selected from a particular organ (e.g., the liver) and can be conditioned to perform one or more functions of that organ such as filtering, secretion of proteins, etc. For example, the cells can be hepatocytes conditioned to secrete various plasma proteins such as albumin, or various digestive compounds such as bile. The circuit can include multiple reactors each with a different cell type conditioned to perform one or more functions of different organs, e.g., hepatocytes for the liver, islets of Langerhans for the pancreas, nephrons for the kidney, bone marrow cells etc. In this way, the circuit can be constructed to simulate multiple organs (e.g., the liver, kidney, etc.), or organ systems (e.g., Gastrointestinal (GI) system) or even multiple organ systems. Cells can be pre-added to the bio-reactors at the factory and shipped in a cooled or other suspended state or they can be added to the bio-reactor by the end user.

In many embodiments, the circuit can comprise a disposable portion such as a cartridge that engages with a fixed portion such as a chassis. The cartridge can be fabricated from one or more moldable plastics known in the art. The bio-reactors can be attached within the cartridge or can be formed into the cartridge using molding or other like methods. Desirably, the cartridge is removably engagable with the chassis, though fixed embodiments are also contemplated. For example, the cartridge can be configured to be placed on the top surface of the chassis so that one or more ports and other fittings align with corresponding features on the chassis. Accordingly, the cartridge can also include one or more locating and/or mating features such as a pin, protrusion, fitting, snap fitting or hole that mate with or otherwise engage a corresponding feature on the chassis.

Typically, the cartridge is sealed and will include inlet and outlet ports so as to connect to the circulating pump, a reservoir containing nutrient solution, another reservoir containing a dialysate or other solutions as well as oxygen or other gas source. Embodiments with an open cartridge are also contemplated. The ports can have one or more control valves which can be mechanically or electrically actuated by the chassis and/or an electronic controller. The cartridge can also include one or more flow conduits to carry nutrient solution to and from each bio-reactor as well as fluidically couple the bio-reactors to the pump and couple the bio-reactors to each other. The flow conduits can comprise channels formed in the cartridge (e.g., by molding) or tubing positioned within the cartridge. The flow conduits are also desirably coupled to the cartridge inlet and outlet ports to carry nutrient solution in and out of the cartridge. In particular embodiments, each bio-reactor has its own inlet and outlet port. In such embodiments, the bio-reactor inlet and outlet ports can be coupled to an inlet and outlet manifold or similar fitting which mates with the chassis. This allows for parallel flow through all or selected number of the bio-reactors. The bio-reactors can also be formed in the cartridge for example by molding or other like method.

In some embodiments, the pump can actually be contained in the cartridge and can be mechanically, electrically, magnetically or pneumatically coupled to a drive unit which can be integral with the chassis or configured as a separate component. A similar arrangement can be used for a mixing device placed within the bio-reactors and or the cartridge.

As described above, the chassis is configured to hold or otherwise engage the cartridge and thus can include one or more locating and/or mating features to locate and engage the cartridge. In particular embodiments, the locating and/or mating feature can comprise a well for the bio-reactor or other portion of the cartridge. Wells can also be used for embodiments having standalone bio-reactors which fit directly onto the chassis. This allows the user to configure a circuit of their choosing. For embodiments not having a cartridge, the chassis can include various features and devices to allow standalone operation of the bio-reactor circuit including, tubing or other flow conduits, inlet and outlet ports and other various fittings, a heater and/or cooler, temperature or other sensors, a mixer and/or pump drive unit and mechanisms for actuating control valves on the cartridge. The chassis can also include the nutrient solution reservoir or contain fittings for coupling to the nutrient solution reservoir and/or fittings and valves for coupling to a compressed gas source such as an oxygen source for oxygenating the nutrient solution. In one embodiment, the drive unit can comprise a magnetic clutch to engage a magnetic pump in one or more of the bio-reactors.

In particular embodiments, the chassis can comprise a table structure where the cartridge is positioned on the top of the table. In such embodiments, the chassis can include one or more wells or other features to allow for the placement and location of the cartridge onto the chassis. The table can include one or more fittings which attach to the sides of the chassis to allow for hook-up to the nutrient solution or other reservoir as well as an oxygen or other compressed gas source.

In various method embodiments, the bio-reactor circuit can be used as an in-vitro test bed to study the effects of different treatments on target cells from one or more organ systems of the body. For example, the bio-reactor can be used to study the effects of various drugs (or other agents) on different organ systems of the body including the hormonal response of such systems, for example, the production of insulin by pancreatic cells. This can be done by adding the drug to the nutrient solution circulating within the circuit or delivering it directly to a particular bio reactor (e.g., by injection). Each reactor and/or the circuit can also include one or more sampling ports for removing samples to analyze cells, secreted hormones as well as add new cells. Also, the circuit can include one or more sensors for making various physiological measurements (e.g., $PO_2$, $CO_2$, glucose, etc.) as well as measuring various metabolic rates and cell outputs (e.g., hormones, glucose uptake, etc.). Additional reactors can be coupled to the circuit as needed to approximate in vivo responses of the whole body or of a selected organ system (e.g., the GI system). The circuit can also include bio-reactors containing various tumor cells (e.g., benign and cancerous cells) to simulate a tumor in a particular organ. A circuit including such tumor bio-reactors can be used as an in vitro test bed to simulate and study the in vivo effects of various drugs and other treatments in treating the tumor while concurrently studying their effects on other organs systems (e.g., toxicity and other metabolic effects). This allows the circuit to be used as a test bed to study both the efficacy and the toxicity and side effects of various drugs and other treatments while the tumor or other target cells are exposed to simulated circulation including exposure to secreted compounds from other organs. Such studies can be further facilitated by coupling selected bio-reactors to a collection reservoir to collect the output of cells in a particular bio-reactor. For example, a bio reactor containing renal cells selected to facilitate renal function can be connected to a reservoir to collect the dialysate from those cells. In this way, the user can quantitatively assess the aggregate physiological function of the cells in the bio-reactor and in turn, the effects of the drug or other treatment on those cells and the organ they simulate. In other embodiments, the circuit can include two or more bio-reactors containing the desired target cell, with one bio-reactor receiving treatment (e.g., in the form of a drug that is injected or otherwise only delivered to that bio-reactor) and the other acting as a control. In this way, side-by-side tests of a treatment and control bio-reactor can be conducted where both are exposed to nearly the same conditions (e.g., the same nutrient solution and compounds produced by cells from other bio-reactors in the circuit) and thus factor out/minimize experimental variation. This reduced variation will in turn lead to a more accurate and precise experimental result.

In addition to tumor cells, other cells can be used as target cells for studying the effectiveness of treatment on a disease or condition. In various embodiments, cells expressing one or more genes contributing to various diseases or conditions can also be employed as a target cell. Target cells can be chosen which have or lack one or more genes responsible for the under production, over production or defective production of one or more proteins (under production can be achieved by the total lack of a gene or the use of an inoperative or knock out gene). For example, pancreatic cells can be used which have knock out genes resulting in a decreased production of insulin contributing to diabetic symptoms. Other cells which have genes causing production or over-production of β-amyloid precursor proteins contributing to Alzheimer' disease can also be used as well as cells having genes responsible for the defective production of surfactant contributing to cystic fibrosis symptoms. Cells having genes responsible for symptoms of other diseases and conditions are also contemplated. Additionally, cells infected with one or more viruses, such as the HIV virus, can also be used as target cells.

In other approaches for studying the physiological effects on the cell type of a particular bio-reactor, the cartridge or the chassis can contain a plurality of optical sensors and emitters positioned adjacent each bio-reactor. The sensors and emitters can be used to perform both qualitative and quantitative measurements of the function and viability of the cells in each bio-reactor including the production of biochemical compounds by the cells. For example, a combination optical emitter/detector device can be used to perform turbidity measurements within the bio-reactor to determine the number of cells in each bio-reactor and/or provide an optical density measurement providing an indication of the change in the number of viable cells in each bio-reactor. In related embodiments, cells types can be selected which fluoresce when exposed to a particular wavelength (e.g., through the use of genetic engineering methods). In this case, an emitter/detector device can be used to measure the amount of fluorescence which in turn, provides an indication of the number of viable cells within the bio-reactor.

In still other embodiments, cells types can be selected which actually emit light continuously or in response to a physiological event such as when their receptors become bound by a protein or other molecule. In this case, an optical detection device (such as a photomultiplier) can be used to measure the amount of emitted light. The amount of emitted light can be used to provide both a qualitative and quantitative indication of the number of viable cells and/or the physiologic function of the cells. For example, cells can be selected which emit light when their receptors bind to a particular compound or group of compounds (e.g., a drug, hormone or other signaling compound). In these and related embodiments, an array of optical sensors can be positioned adjacent each bio-reactor so as to measure the aggregate optical output and thus function of the cells in the bio-reactor.

Further details of these and other embodiments and aspects of the invention are described more fully below, with reference to the attached drawing figures.

DETAILED DESCRIPTION OF THE INVENTION

Figure 1A:
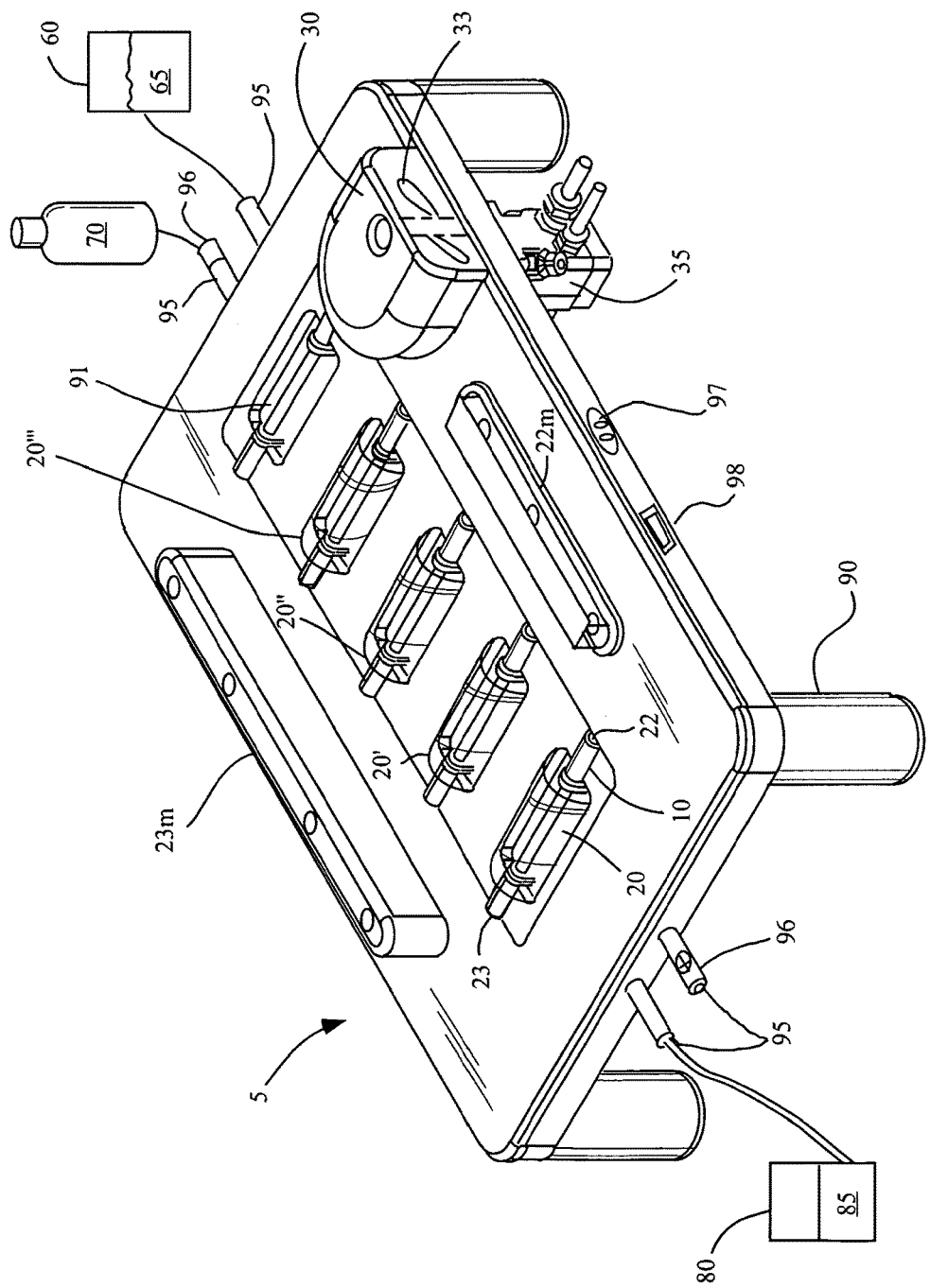
FIG. 1a is a perspective view of a bio-reactor circuit including one or more bio-reactors and a chassis according to an embodiment of the invention.
Figure 1B:
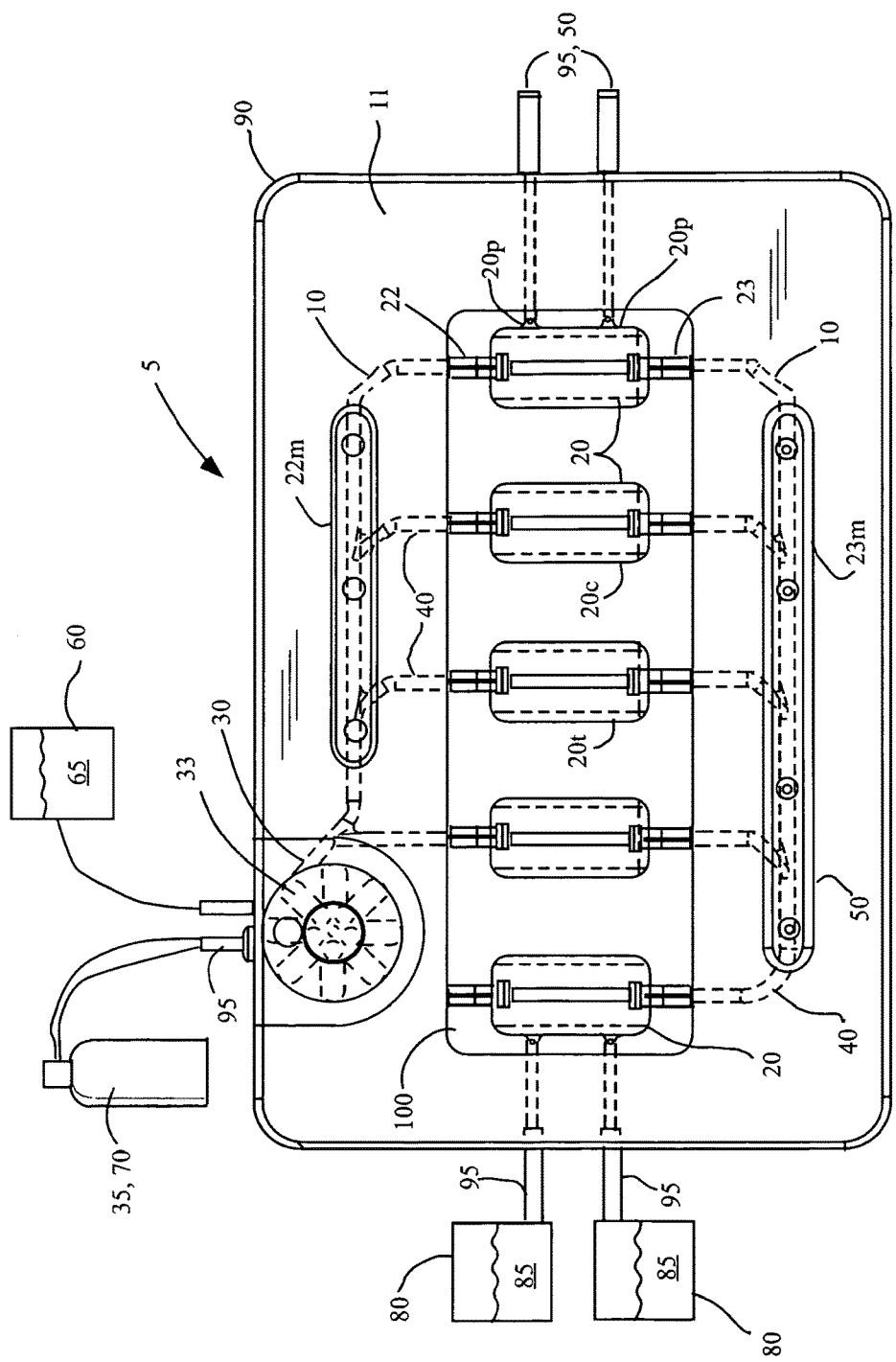
FIG. 1b is a top/schematic view of an embodiment of a bio-reactor circuit including one or more bio-reactors and a chassis.

Referring now to FIGS. 1-5, an embodiment of an in vitro bio-reactor circuit system 5 can include a bio-reactor circuit 10 including one or more bio-reactors 20, a pump 30, flow conduits 40, one or more ports or fittings 50, a reservoir 60 and an oxygen or other gas source 70. Reservoir 60 will typically be configured for a nutrient other solution 65 which is circulated through the circuit. The circuit can also include collection reservoirs 80 for storage of dialysate 85 or other solution. Bio-reactors 20 can be arranged in a parallel or serial fashion or a combination thereof. In many embodiment, circuit 10 can include a first and a second and third bio-reactor 20', 20" and 20''' with additional numbers also contemplated. As is discussed below, all or a portion of the circuit can be contained in a cartridge 100 that engages with a chassis 90.

Pump 30 serves to circulate solution 65 through circuit 10 in either in a continuous or pulsatile fashion or a combination. Accordingly in various embodiments, pump 30 can comprise a continuous or peristaltic pump known in the art. In particular pulsatile flow embodiments, pump 30 can be configured to simulate cardiac circulation both in terms of flow rate and pressure ranges (e.g., typical diastolic and systolic pressure ranges, e.g., 80 to 120 mmHg). Pump 30 can be electronically controlled and can be entirely self-contained both in terms of a pumping mechanism 33 and drive unit or can also include a separate drive unit 35. Drive unit 35 can be mechanical, hydraulic, pneumatic or magnetic. In some embodiments, pumping mechanism 33 can be contained in cartridge 90 and drive unit 35 can be positioned on chassis 90. In such embodiments, the pumping mechanism 33 can be coupled to drive unit 35 through a magnetic clutch known in the art. In other embodiments, a mixing device 34 such as a magnetic stirring device can be positioned in various locations in the circuit including in one or more of the bio-reactors or reservoirs. In related embodiments one or more bio-reactors 20 can include a dedicated mixing device or even a pump or pump mechanism. In this way, flow to a particular bio-reactor can be adjusted (manually or automatically) depending upon one or more experimental parameters.

Figure 3A:
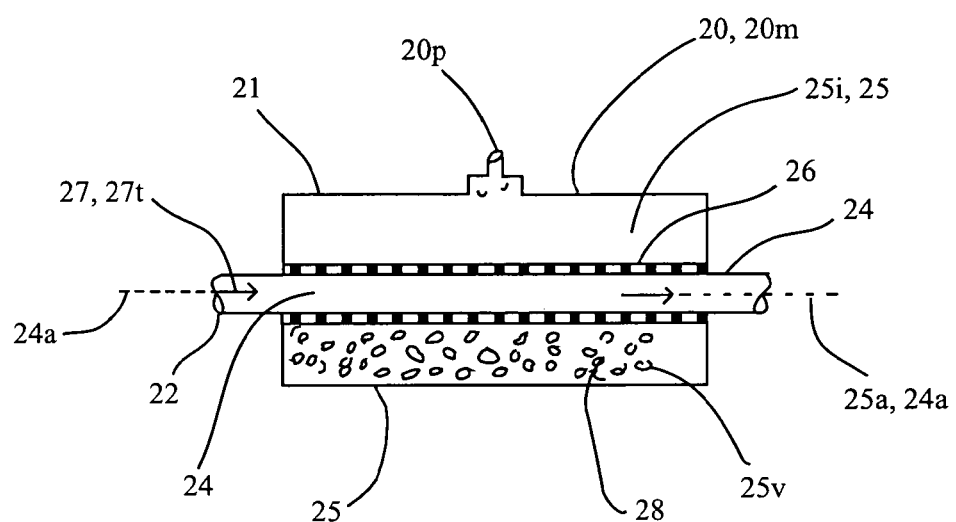
FIG. 3a is a lateral view of an embodiment of a bio-reactor.

In various embodiments, bio-reactor 20 can comprise a multi chamber structure 20m that includes chambers for maintaining a selected group of cells as well as performing other functions. In many embodiments, bio-reactor 20 can comprise a housing 21 having an inlet 22 and outlet port 23 and at least a first chamber 24 and second chamber 25 as is shown in FIG. 3a. Additional chambers are also contemplated. The chambers are separated by a porous membrane 26 allowing for diffusion of gases and liquids between the chambers. The first chamber provides a flow path 27 for a nutrient or other solution 65 flowing through the bio-reactor and thus is also referred to as flow chamber 24. The second chamber 25 provides a volume 25v for maintaining the viability of cells 28 and thus is also referred to as a cell chamber 25. Cells 28 can produce compounds 28c which can collect in chamber 25 and diffuse across membrane 26. Typically, cells 28 will be cells isolated from one or more organs or other locations in the body and can also comprise various isolated tumor cells. In some embodiments, inlet and outlet ports 22 and 23 can be coupled to inlet and outlet manifolds 22m and 23m described herein.

Bio-reactor 20 can also include one or more access or sampling ports 20p and sensors 20s. Sampling ports 20p can be used for removing samples to analyze cells, secreted hormones etc., as well as add new cells. Sensors 20s can include various thermal, optical and chemical sensors and can be used for making various physiological measurements (e.g., $PO_2$, $CO_2$, glucose, etc.) as well as measuring various metabolic rates and cell outputs (e.g., hormones, glucose uptake, etc.). Suitable sensors 20s can include thermisters, FETs photomultipliers, strain gauges, mems based and electrode sensors.

Figure 4A:
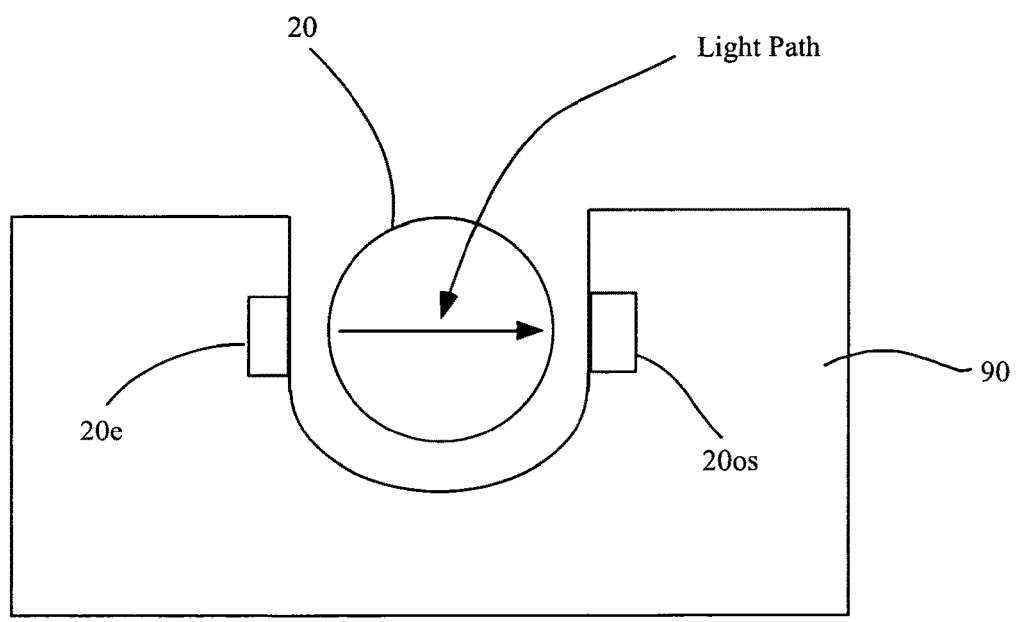
FIG. 4a is a cross-sectional view of a configuration for making an optical density/turbidity measurement through the bio-reactor.
Figure 4B:
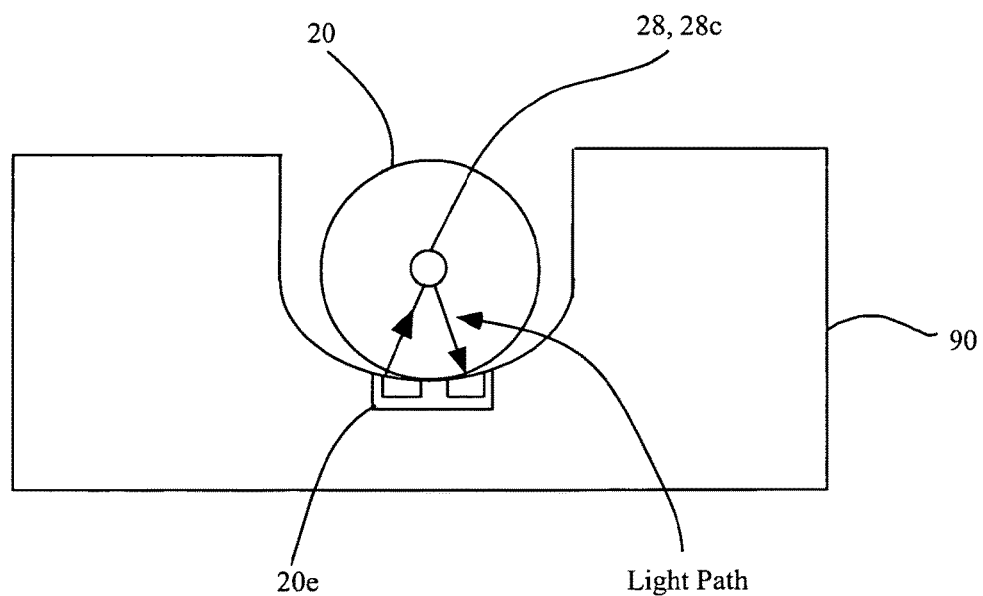
FIG. 4b is a cross-sectional view of a configuration for making a reflectance measurement of the interior of the bio-reactor.

In various embodiments, bio-reactors 20 can include a combination of optical sensors 20os and emitters 20e that are configured for making one or more optical measurements. In particular embodiments, one or more sensors and emitters 20os and 20e can be positioned on, in or adjacent one or more selected bio-reactors 20. The sensors and emitters can be used to perform both qualitative and quantitative measurements of the function and viability of the cells in each bio-reactor including the production of biochemical compounds by the cells. For example, a combination of optical emitters 20e (such as a diode or like device) and sensors 20so can be arranged about the bio-reactor in a linear or similar fashion (as is shown in FIG. 4a) so as to make turbidity and/or absorbance measurements within a bio-reactor 20 to determine the number of cells in each bio-reactor. In other embodiments, an emitter-detector device 20ed configured for making reflectance measurements can be positioned adjacent bio-reactor 20 (as is shown in FIG. 4b) so as to make reflectance measurements of solution within the bio-reactor. Such measurement can be used for measuring one or more analytes within the bio-reactor such as glucose or one or more compounds 28c produced by cells 28.

Figure 4C:
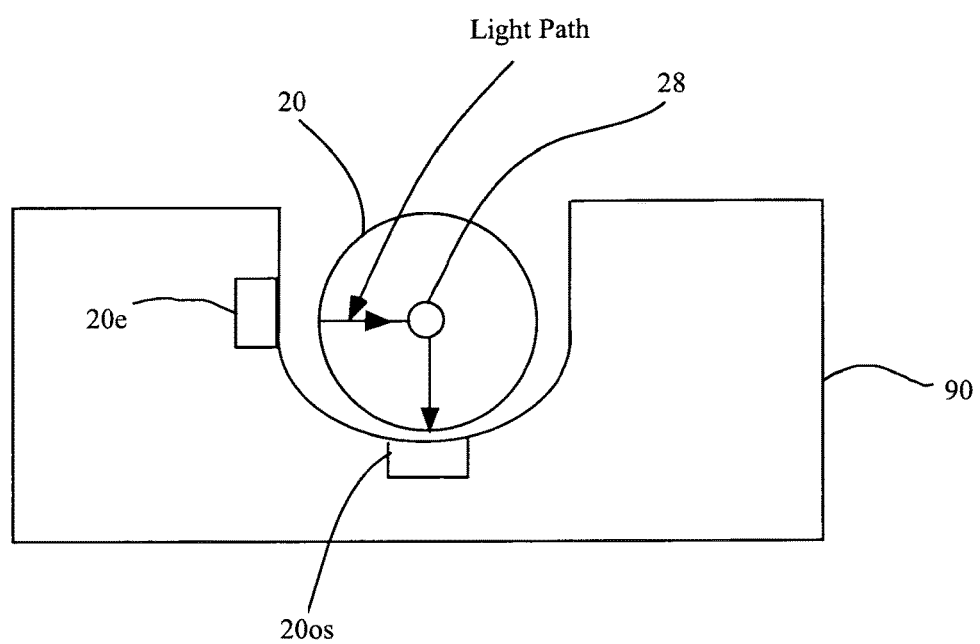
FIG. 4c is a cross-sectional view of a configuration for making a fluorescence measurement of the bio-reactor.

In still other embodiments, cells 28 can be selected which fluoresce when exposed to a particular wavelength (e.g., through the use of genetic engineering methods). In this case, one or more optical emitters or emitters 20e and optical sensors/detectors 20os can be positioned adjacent bio-reactor 20 (as is shown in FIG. 4c) so as to measure the amount of fluorescence by cells 28. Measurement of such fluorescence provides an indication of the number of viable cells within the bio-reactor and/or an indication of their physiologic state (e.g., whether a receptor has been bound by a protein such as a G-protein). Typically, the working portions of emitters 20e and detectors 20os will be positioned at about a 90° angle with respect to each other and the exterior of bio-reactor housing 21 so as to minimize the amount of optical signal traveling directly from emitter 20e and detector 20os and so only detect signal due to actual cell fluorescence.

Figure 4D:
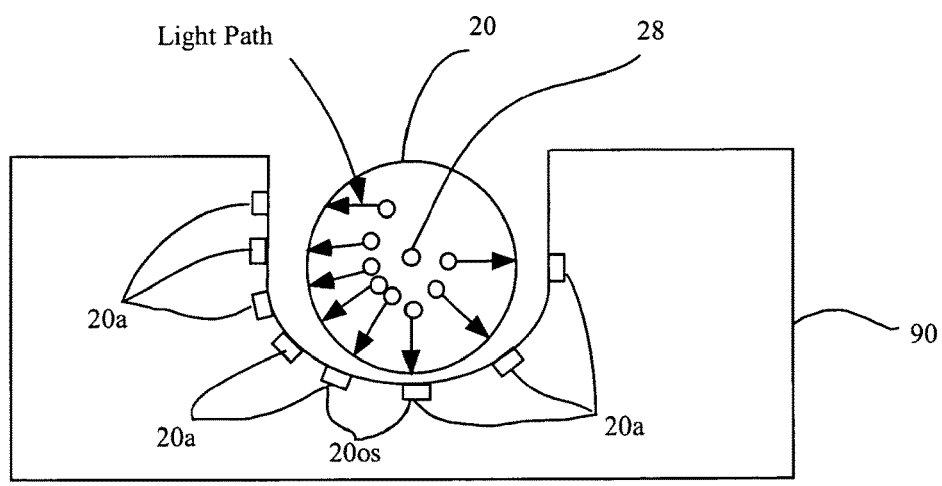
FIG. 4d is a cross-sectional view of a configuration including an array of optical sensors for making optical measurements within the bio-reactor.

In still other embodiments, cells types 28 can be selected which actually emit light or emit light in response to a physiological event such as when their receptors become bound by a protein. In this case, an optical sensor 20os (such as a photomultiplier) can be used to measure the amount of emitted light. The amount of emitted light can be used to provide both a qualitative and quantitative indication of the number of viable cells 28 and/or the physiologic function of the cells. For example, cells 28 can be selected which emit light when their receptors bind to a particular compound or group of compounds (e.g., a drug, hormone, or other signaling compound). In these and related embodiments, an array 20a of optical sensors 20os can be positioned adjacent selected a bio-reactor 20 (as is shown in FIG. 4d) as to measure the aggregate optical output of cells 28 in bio-reactor 20 and thus, their aggregate metabolic/physiologic function.

Figures 3B, 3C:
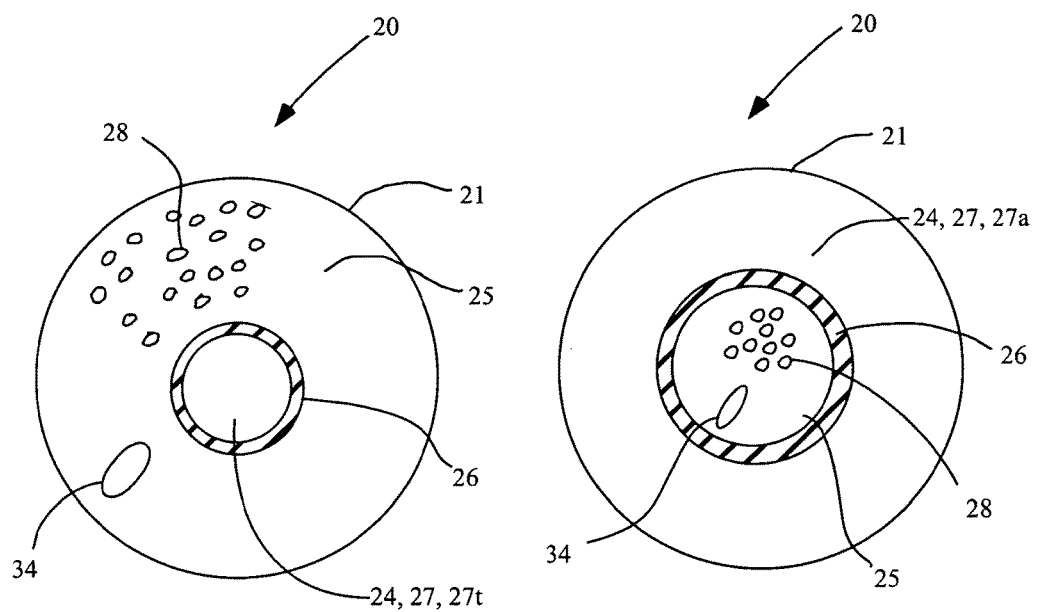
FIG. 3b is a cross-sectional view of an embodiment of a two chamber bio-reactor including a tubular flow path.
FIG. 3c is a cross-sectional view of an embodiment of a two chamber bio-reactor including an annular flow path.

In preferred embodiments, first chamber 24 is substantially tubular and second chamber 25 surrounds first chamber 24 and is substantially annular as is shown in FIGS. 3a and 3b. Other shapes are also contemplated. Preferably, chambers 24 and 25 are substantially co-axial (e.g., they have a common longitudinal axis 24a and 25a), though non-coaxial configuration are also contemplated. This configuration allows for a tubular central flow path 27t for the flow of nutrient solution 65 through first chamber 24 which in turn allows for the outward diffusion of nutrients and gases from nutrient solution 65 across membrane 26 and into second chamber 25. It also provides for the diffusion of compound 28c and cellular waste products and gases (e.g., $CO_2$) from chamber 25 across the membrane into chamber 24. Diffusion can also be facilitated by placement of a mixing device 34 placed in chamber 25 as is shown in FIG. 3b. Mixing device 34 can include various magnetically actuated mixing devices such as a magnetic stir rod or like device.

Figure 3D:
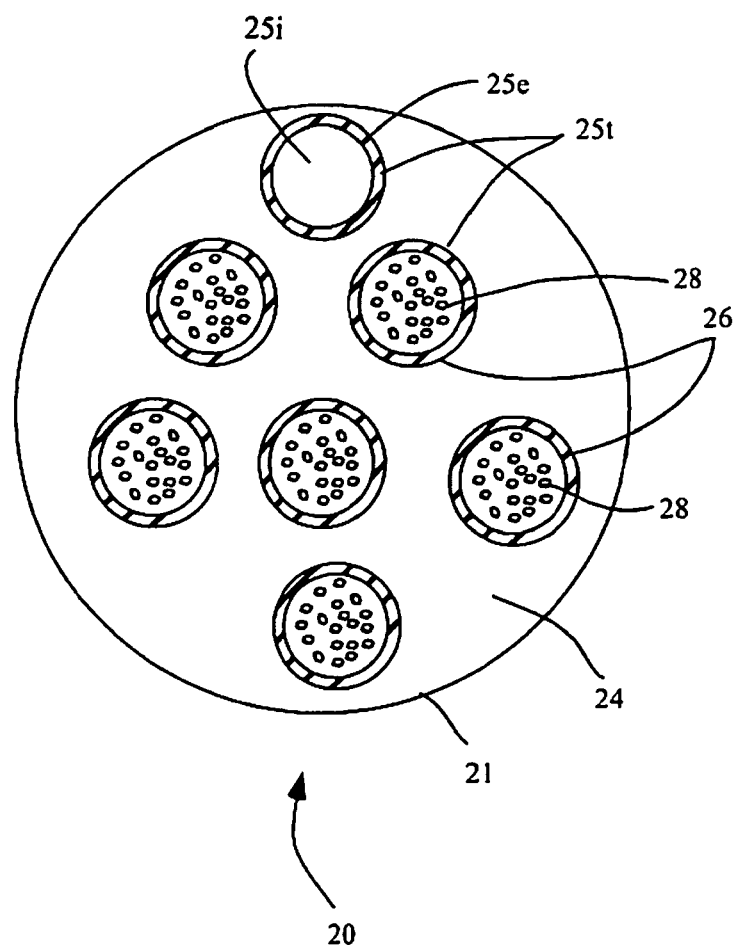
FIG. 3d is a cross-sectional view of an embodiment of a bio-reactor having a plurality of hollow fiber membranes.
Figure 3E:
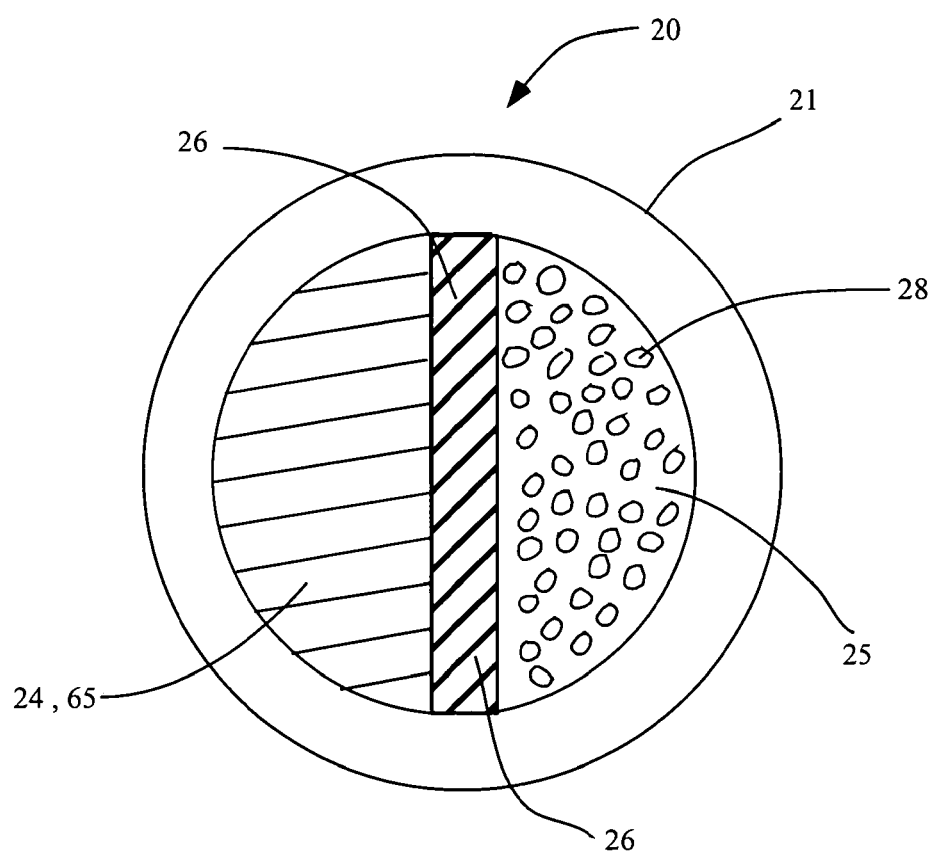
FIG. 3e is a cross-sectional view of an embodiment of a two chamber bio-reactor including a semi-circular flow path.

Various embodiments of the bio-reactor can also include a reverse configuration whereby first chamber 24 is annular and substantially surrounds second chamber 25 as is shown in FIG. 3c. This results in an annular flow path 27a. In such embodiments, chamber 25 can include a mixing device 34 such as a magnetically actuated mixing device. In other related embodiments, second chamber 25 can comprise a plurality of tubular membrane structures 25t with cells 28 positioned in their interior 25i and nutrient solution 65 flowing over their exterior surface 25e in chamber 24 as is shown in FIG. 3e. In these embodiments, membrane 26 can include various hollow fiber membrane materials known in the art including polysulfone, polyacrylonitrile, cellulose acetate, polypropylene, PTFE, polyethylene (including ultra high molecular polyethylene) based membranes and combinations thereof. In other embodiments, chambers 24 and 25 can be side by side for example, having a semi-circular or "D" shape in which they are separated by membrane 26 which functions as a dividing wall between the chambers as is shown in FIG. 3d. Still other chamber shapes and arrangements for chambers 24 and 25 are also contemplated such as a crescent shape. In various embodiments, the shape and arrangement of the chambers can be matched to the particular cell line and/or organ to be simulated.

Figure 3F:
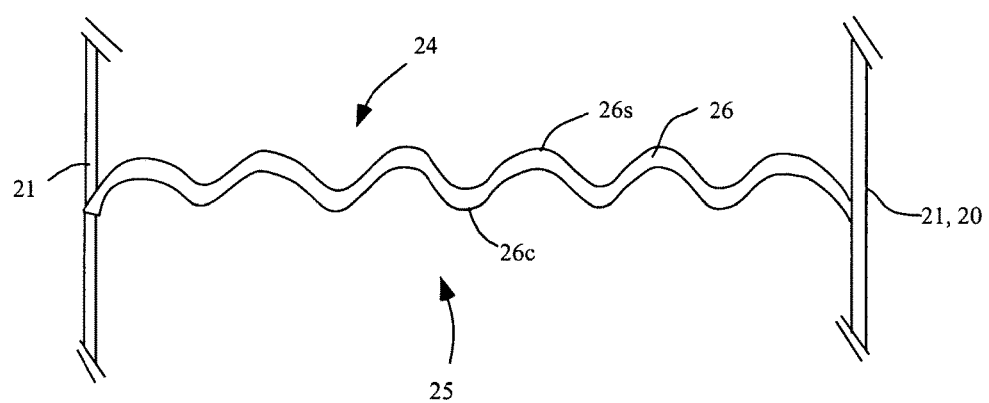
FIG. 3f is a lateral view illustrating an embodiment of a bio-reactor membrane having a convoluted surface.

Membrane 26 can be fabricated from various membrane materials known in the art including PTFE, NYLON, polysulfone, polyacrylonitrile, cellulose acetate, PET, polyester, polypropylene, polyethylene (including ultra high molecular polyethylene) based membranes and combinations thereof. The membrane 26 is desirably configured to allow for the diffusion of compound 28c from the second chamber 25 into first chamber 24 and flow path 27 as well as allow for the diffusion of gases, nutrients and other biochemical compounds (e.g., drugs, hormones and like compounds) into and out of the second chamber 25. Diffusion can be enhanced by configuring the surface 26s of membrane 26 to have a convoluted or other curved shape 26c to increase the surface area available for diffusion and break down boundary layers as is shown in FIG. 3f. Diffusion in both directions through the membrane can also be enhanced by configuring the flow of solution 65 through chamber 24 such that maximum concentration gradients are maintained across the membrane and boundary layer effects are minimized. For diffusion from chamber 25 into 24, diffusion can be enhanced by maintaining sufficient flow or sweep of solution 65 or other liquid such that boundary layers in chamber 24 containing concentrations of compounds diffusing from chamber 25 into 24 are swept away so as to maintain maximum concentration gradients across the membrane and in turn maximum diffusion driving forces. Similarly, for diffusion from chamber 24 into 25, sufficient flow through chamber 24 can be maintained to sweep away boundary layers responsible for concentration polarization effects due to the build up of boundary layers containing concentrations of compounds having lesser amounts of diffusion across membrane 26 (e.g., due to reduced permeability within the membrane).

Figure 3G:
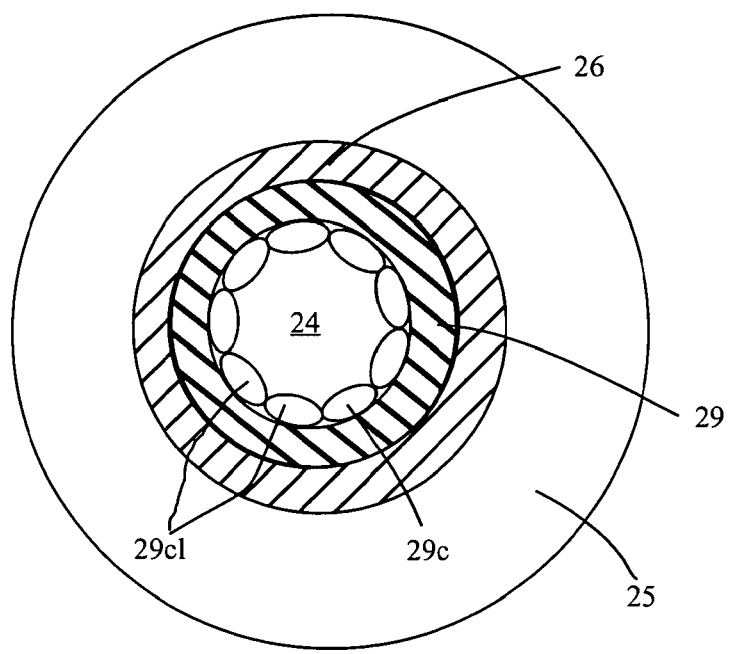
FIG. 3g is a cross-sectional view illustrating an embodiment of a bio-reactor membrane having a coating for the attachment of endothelial cells.

In many embodiments, membrane 26 can include a coating 29 which has a cell binding affinity for the attachment of endothelial cells 29c (or other like cells) to the coating as is shown in FIG. 3g. Cell binding affinity, as used herein, means the ability to attach to a particular cell, such as an endothelial cell, but not exclusively to that cell. Desirably, the cell binding affinity of the coating is configured to promote the attachment and proliferation of sufficient endothelial cells to cover the coating and form a substantially confluent layer of cells 29cl. Determination of the cell coverage can be performed by microscopic observation using standard cell staining and observational/quantitative techniques known in the art. Coating 29 can include various extracellular matrix materials known in the art including various collagens. In various embodiments, coating 29 can comprise various polypeptides that include cell binding domains for specific attachment to endothelial cells. In preferred embodiments, coating 29 comprises polypeptide molecules that have such cell binding sites for attachment to endothelial cells, but have a peptide length such that they are not degraded in vivo by proteases or like molecules and thus can remain attached to a surface in vivo for extended time periods (e.g., days, months or even years). Specific preferred embodiments for coating 29 can include a 15 amino acid length poly-peptide known as P-15 comprising the amino acid sequence Gly-Thr-Pro-Gly-Pro-Gln-Gly-Ile-Ala-Gly-Gln-Arg-Gly-Val-Val (SEQ ID NO:1) as well as variants thereof. Other preferred embodiments of coating 29 can include multi-arm polypeptides (MAP) compounds having enhanced cell binding properties including a MAP compound comprising multiple P-15 sequences. In these and related embodiments, coating 29 can be covalently bound to surface 26s of membrane 26. Further description of suitable MAP compounds including MAP compounds comprising P-15 is found in U.S. patent application Ser. No. 10/664,697, entitled Multiple-arm peptide compounds, methods of manufacture and use in therapy, filed Sep. 16, 2003 which is fully incorporated herein by reference.

In various embodiments of a method for coating application, the coating can be applied through a combination of plasma treatment of membrane 26, treatment with chemical activating agents such as a combination of sodium hydroxide and chloroacetic acid and subsequent treatment with a coating solution to covalently bind the coating to the membrane surface. Further description of P-15 including methods of its manufacture and attachment to surfaces, is found in a paper by Cheng Li, Arthur Hill and Mir Imran, entitled, "In vitro and in vivo studies of ePTFE vascular grafts treated with P15 peptide", Journal of Biomaterials Science, Polymer Edition, Volume 16, Number 7, 2005, pp. 875-891(17) which is fully incorporated by reference herein.

In various embodiments of a method for attaching endothelial or other like cells to membrane 26, the bio-reactor 20 including membrane 26 can be filled with a nutrient solution containing endothelial cells or other like cells and then incubated at temperature (e.g., 37° C.) for 4 hours or more with agitation to allow the cells to be washed over and attach to membrane surface 26s. The seeded bio-reactor can then be connected to the bio-reactor circuit 10 and have a heated nutrient solution circulated through the bio-reactor for 12 to 24 hours to allow the attached cells to spread and proliferate over the membrane surface 26s. Alternatively, an endothelial nutrient solution can be directly circulated through bio-reactor connected to a bio-reactor circuit so as to allow endothelial cells to attach, spread and proliferate over the surface. The concentration of endothelial cells and periods for incubation and circulation can be adjusted depending upon the selected membrane coating, membrane material and membrane surface area. For example, longer periods can be selected for membranes having larger amounts of surface area.

In various embodiments, cells 28 disposed in second chamber 25 can be selected and/or conditioned to perform one or more functions. For example, the cells can be selected from a particular organ and can be conditioned to perform one or more functions of that organ such as filtering, secretion of proteins, etc. For example, the cells can be hepatocytes conditioned to secrete various plasma proteins such as, albumin, or various digestive compounds such as bile. Conditioning can be achieved by exposing the cells to various nutrient solutions and other conditioning factors such as VGEF and various hormones. Circuit 10 can include multiple reactors 20 each with a different cell type 28 conditioned to perform one or more functions of different organs, e.g., hepatocytes for the liver, islets of Langerhans for the pancreas, nephrons for the kidney, bone marrow cells etc. In this way, circuit 10 can be constructed to simulate multiple organs (e.g., the liver, kidney, etc.), or organ systems (e.g., GI system) or even multiple organ systems. In various embodiments, cells 28 can include hepatic, pancreatic, renal, myocardial, neuronal, bone and stem cells including hematopoietic and mesenchymal cells. Cells 28 can also include various tumor cells (benign or cancerous) which are selected to study the effects of various treatments. Cells 28 can be pre-added to the bio-reactors at the factory and shipped in a cooled or other suspended state or they can be added to the bio-reactor by the end user.

Figure 1C:
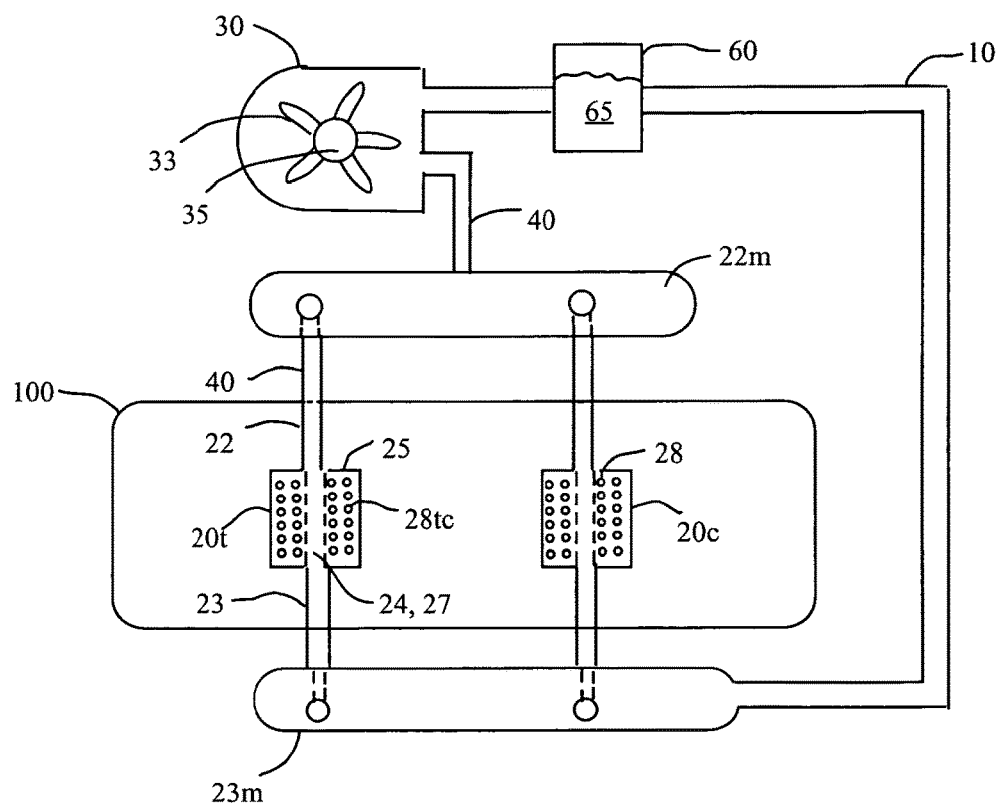
FIG. 1c is a top/schematic view of an embodiment of a bio-reactor circuit including control and treatment bio-reactors.

In various methods of use, bio-reactor circuit 10 can be used as an in-vitro test bed 11, to study the effects of various treatments on target cells 28tc from one or more organ systems of the body. For example, the bio-reactor can be used to study the effects of various drugs or other agents on different organ systems of the body including the hormonal response of such systems (e.g., the production of insulin by pancreatic cells). This can be done by adding the drug to the nutrient solution circulating within circuit 10 or injecting it into a particular bio reactor. This can be done through one or more sampling ports 20p. These same ports can be used to withdraw samples of cells and liquid samples to test for the presence of biochemical compounds 28c. Also, circuit 10 including bio-reactor 20 can include one or more sensors 20s for making various physiological measurements (e.g., $PO_2$, $CO_2$, glucose, etc.) as well as measuring various metabolic rates and cell outputs (e.g., hormones, glucose uptake, etc.). Additional bio-reactors can be coupled to the circuit as needed to approximate in vivo responses of the whole body or of a selected organ system (e.g., the GI system). The circuit can also include bio reactors containing various tumor cells (e.g., benign and cancerous cells) to simulate a tumor in a particular organ. A circuit including such tumor bio-reactors can be used as an in vitro test bed to simulate and study the in vivo effects of various drugs and other treatments in treating the tumor while concurrently studying their effects on other organ systems as well (e.g., toxicity and other metabolic effects). This allows the circuit to be used as a test bed to study both the efficacy and the toxicity and side effects of various drugs and other treatments while the tumor or other target cells 28tc are exposed to simulated circulation including exposure to secreted compounds from other organs. Such studies can be further facilitated by coupling selected bio-reactors to a collection reservoir 80 to collect the output of cells in a particular bio-reactor. For example, a bio reactor containing renal cells selected to facilitate renal function can be connected to a reservoir to collect the dialysate from those cells. In this way, the user can quantitatively assess the aggregate physiological function of the cells in the bio-reactor and in turn, the effects of the drug or other treatment on those cells and the organ they simulate. In other embodiments, the circuit can include two or more bio-reactors containing the desired target cell 28tc, with one bio-reactor receiving treatment (e.g., drug injected into the bio-reactor) and thus being a treatment reactor 20t, and then other acting as a control 20c as is shown in FIG. 1c. In this way, side-by-side tests of a treatment 20t and control bio-reactor 20c can be performed where both are exposed to nearly the same conditions (e.g., same nutrient solution, temperature, etc.) and thus factor out/minimize experimental variation. This reduced variation will in turn lead to a more accurate and precise experimental result.

In addition to tumor cells, other cells can be used as target cells 28tc for studying the effectiveness of treatment on a disease or condition. In various embodiments, cells expressing one or more genes contributing to various diseases or conditions can also be employed as a target cell. Target cells can be chosen which have or lack one or more genes responsible for the under production, over production or defective production of one or more proteins (under production can be achieved by the total lack of a gene or the use of an inoperative or knock out gene). For example, pancreatic cells can be used which have knock out genes resulting in a decreased production of insulin contributing to diabetic symptoms. Other cells which have genes causing production or over-production of β-amyloid precursor protein contributing to Alzheimer' disease can also be used as well as cells having genes responsible for the defective production of surfactant contributing to cystic fibrosis symptoms. Cells having genes responsible for symptoms of other diseases and conditions are also contemplated. Additionally, cells infected with one or more viruses, such as the HIV virus, can also be used as target cells 28tc.

Flow conduits 40 serve to carry nutrient and other solutions to and from each bio-reactor 20 as well as fluidically couple the bio-reactors to pump 30, reservoir 60 and couple the bio-reactors to each other. Conduits 40 will typically comprise flexible or other tubing, but for embodiments of the circuit contained in a cartridge they can also comprise channels formed in the cartridge (e.g., by molding). The flow conduits are also desirably coupled to the cartridge inlet and outlet ports to carry nutrient solution in and out of the cartridge. Conduits 40 can be treated with one or more coatings or plasma treatments to enhance wetting and hence fluid flow through the conduit.

Figure 1D:
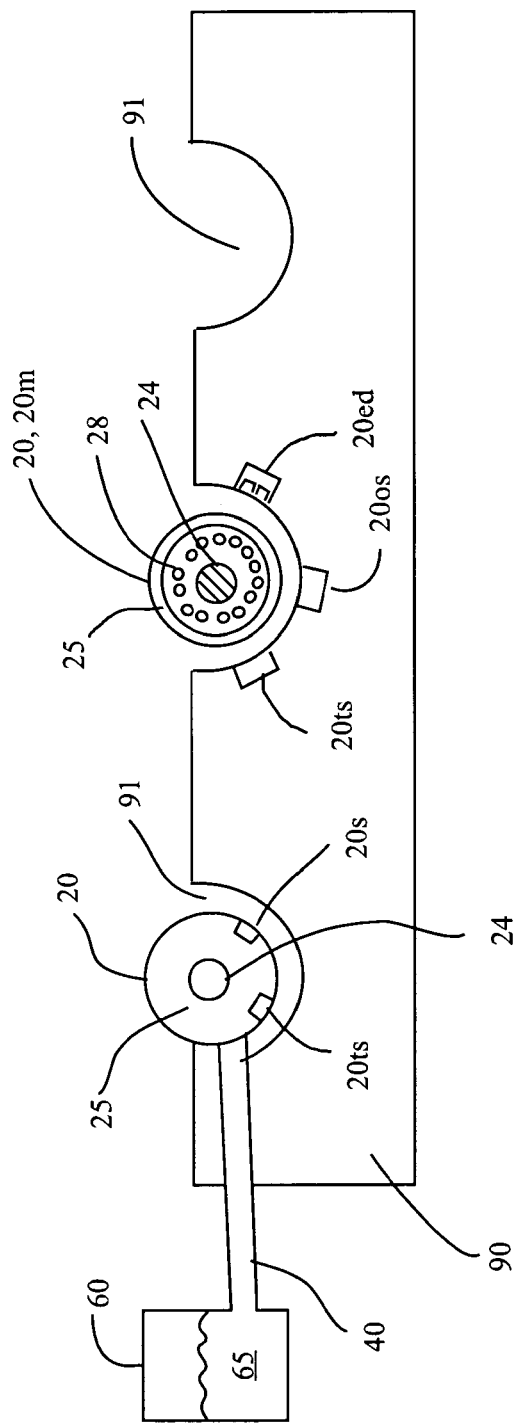
FIG. 1d is a lateral view of a bio-reactor circuit including one or more bio-reactors and a chassis having wells for the bio-reactors and other features.

In many embodiments, all or a portion of the components of circuit 10 can be placed on or otherwise engage a chassis 90 which can a have a table-like structure, though other configurations are also contemplated. Chassis 90 can include one or more fittings 95 which can be configured to be coupled to reservoirs 60 and 80 as well as gas source 70. Fittings 95 can also include one or more valves 96 including check valves or other control valves including an electrically or mechanically actuable control valve such as a solenoid valve. The chassis can also include one or more wells or depressions 91 for the location of bio-reactors 20, flow channels 40 or other feature in bio-reactor circuit 10. The chassis can include sufficient numbers of wells 91 and fittings 95 such that the user can use wells 91 to construct a custom circuit 10 by positioning bio-reactors 20 in a user-selected configuration. The chassis can also include heater and/or cooler devices (not shown) to maintain bio-reactors 20 and/or reservoirs 60 at a selected temperature to either incubate cells 28 in the bio-reactor or to reduce or even suspend their metabolic activity by producing a hypothermic state. In use, such approaches allow for the study of various hypothermic or other temperature control treatments for reducing cell injury after hypoxia and/or ischemia. In these and related embodiments bio-reactors 20 can include one or more temperature sensors 20ts as is shown in the embodiment of FIG. 1d.

Figure 2A:
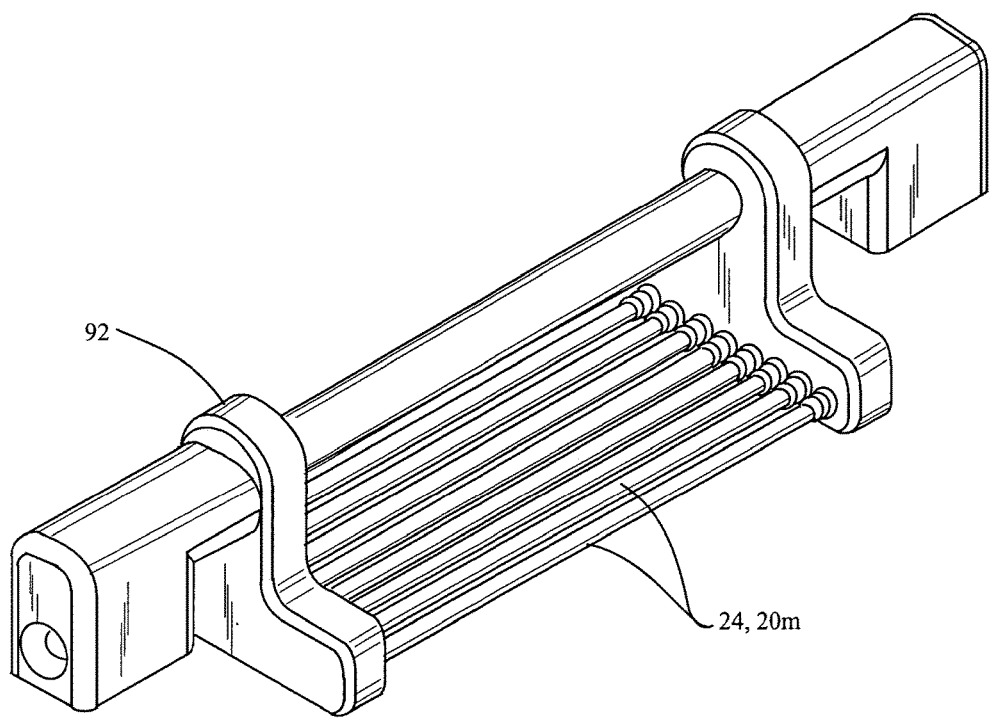
FIG. 2a is a perspective view of an embodiment of a manifold for connection of multiple flow chambers.
Figure 2B:
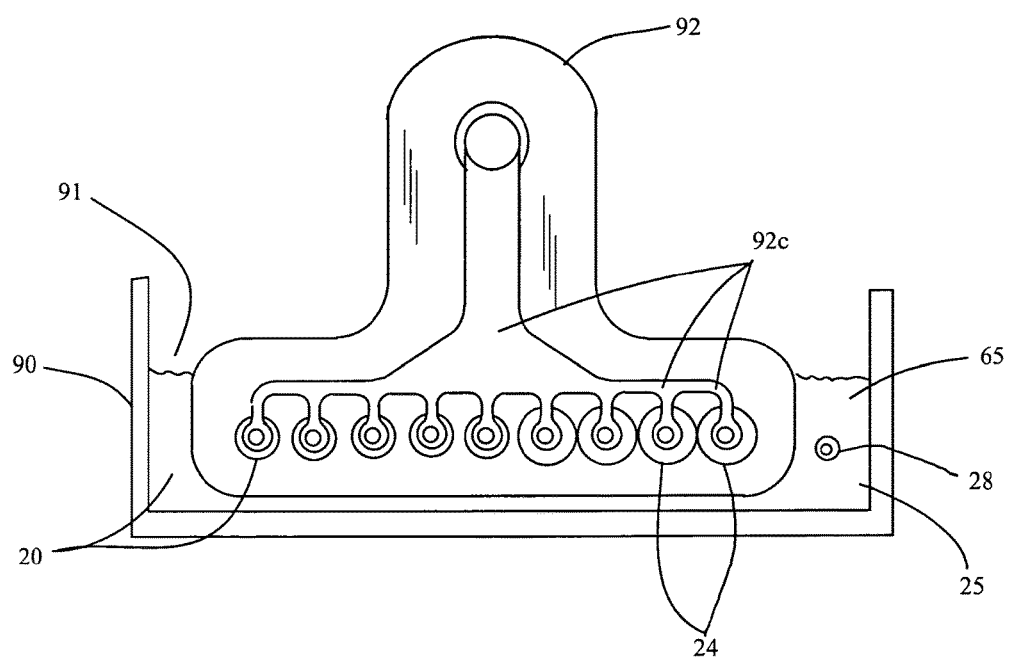
FIG. 2b is a lateral view of an embodiment of a manifold for connection of multiple flow chambers.

In various embodiments, wells 91 can be used to not only locate the bio-reactor 20 but to actually form the bio-reactor. In such embodiments, the well 91 can comprise the second or cell chamber 25 with one or more flow chambers 24, formed from membrane material 26, positioned within the well. Multiple flow chambers 24 can be positioned within each well allowing for an increased amount of membrane surface area for gas exchange within the well. In these and related embodiments, flow chambers 24 can be configured to be removably positioned within each well 91 through means of a well manifold or fitting 92 as is shown in FIGS. 2a and 2b. Well manifold 92 can include internal channels 92c for connection and supplying fluid to each flow chamber 24. In use, well manifold 92, allows for quick connection or disconnection of flow chambers 24 allowing chambers 24 to be readily added or replaced on each bio-reactor 20. This can be beneficial for quick replacement of a given flow chamber should the membrane 26 become fouled or the adherent endothelial cell layer become compromised.

The chassis will also typically include electrical conduits 97 and data ports 98 coupling to an electrical power supply and an external processor based device such as a computer. In various embodiments data ports 98 can comprise a USB port or wireless port such as an RF or infrared based port for wireless signaling to an external computer. Chassis 90 can also include pump 30 or a pump drive unit 35 (which powers pump 30), electrical power supply and/or transformers (not shown) as well as reservoirs 60 and 80 which can be placed above and/or below the chassis for gravity feed. Additionally, in an embodiment having a chassis 90, inlet and outlet ports 22 and 23 can be coupled to inlet and outlet manifolds 22m and 23m or similar fitting which mates with chassis 90. This allows for parallel flow through all or a selected number of the bio-reactors 20 as well as maintaining equal inlet pressures for each bio-reactor so connected.

Figure 5A:
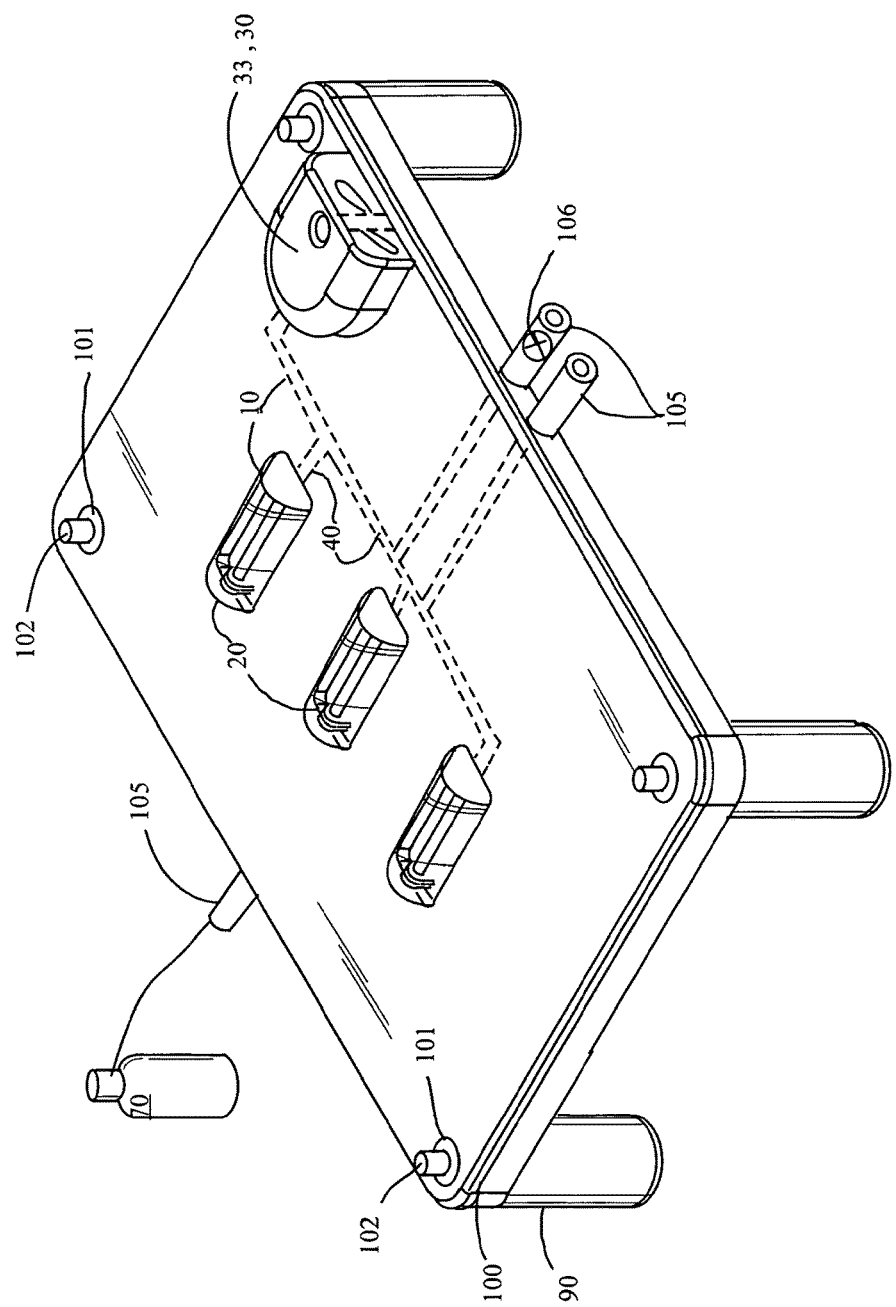
FIG. 5a is a perspective view of an embodiment of a bio-reactor circuit cartridge.
Figure 5B:
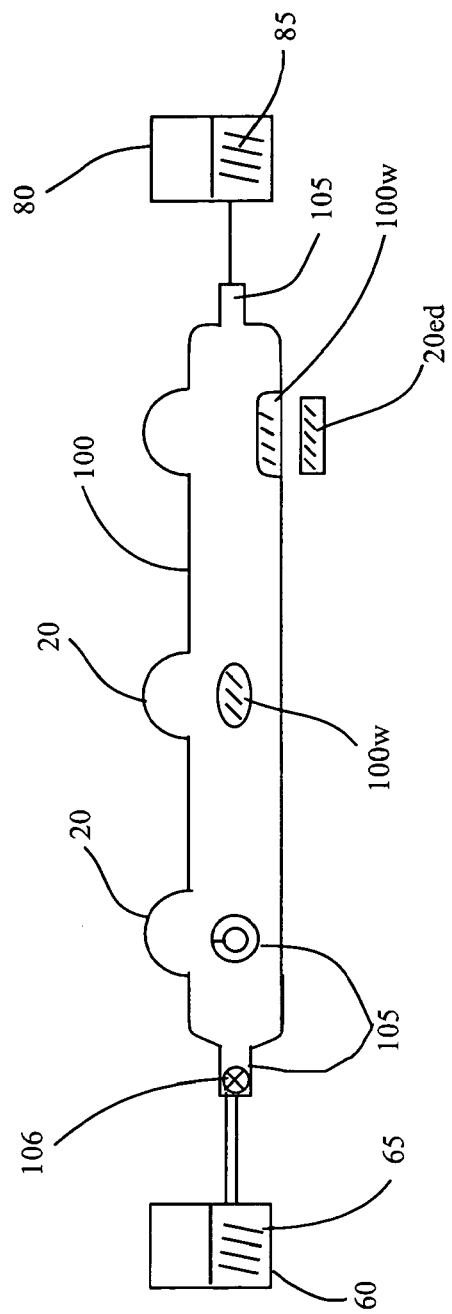
FIG. 5b is a cross sectional view of an embodiment of a bio-reactor circuit cartridge having a sealed configuration.
Figure 5C:
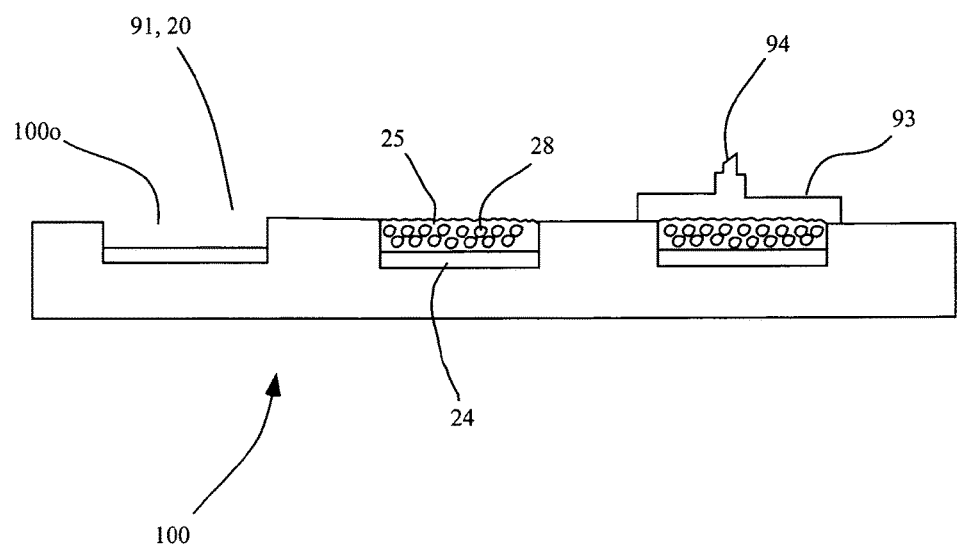
FIG. 5c is a cross sectional view of an embodiment of a bio-reactor circuit cartridge having an open configuration.

Referring now to FIGS. 5a-5c, in many embodiments, all or a portion of bio reactor-circuit 10 can be contained in a cartridge 100 which is desirably removably engageable with chassis 90. Bio-reactors 20 can be formed directly within cartridge 100 or they can be attached by the user, e.g., by means of a snap fitting. Typically, the cartridge will also include fluid conduits 40 and inlet and outlet ports 105 so as to connect bio-reactors 20 to a circulating pump 30, as well as reservoirs 60 and 80 and gas source 70. Ports 105 can have one or more control valves 106 which can be mechanically or electrically actuated by the chassis and/or an electronic controller. In various embodiments, cartridge 100 can include a pumping mechanism 33 such as a magnetically or pneumatically actuated impeller or centrifugal pumping mechanism, or even a complete pump 30.

Cartridge 100 can be fabricated from one or more moldable polymers known in the art including rigid polymer such as polyester, PET, PEEK and acrylic and flexible polymers or elastomers such as polyurethane, and silicones. The cartridge 100 can also be optically transparent and constructed from heat resistant polymers such as polyetherimide to be heat sterilizable. In specific embodiments, the cartridge can include optical viewing windows 100w for transmission of light to and from optical emitters and sensors and such as those contained in an emitter detection device 20ed.

Typically, cartridge 100 will be configured to be placed on the top of chassis 90, but it in alternative embodiments, can also be configured to be inserted. For top placement configurations, the cartridge can include one or more location and/or mating features 101 which are configured to engage a corresponding mating features 102 in chassis 90. Location and mating features 101 and 102 serve to both locate and the cartridge 100 on the chassis 90 as well as removably engage the cartridge with the chassis. In various embodiments, mating features 101 and 102 can include a hole and a pin or other protuberance, as well as various connectable fittings known in the art including various snap fittings.

Typically, cartridge 100 is sealed as is shown in FIG. 5b. However in alternative embodiments, cartridge 100 can have an open configuration 100o as is shown in FIG. 5c. These embodiments allow for open or semi exposed bio-reactors 20 formed within wells 91. Such embodiments allow for direct observation and access to each bio-reactor 20 allowing for direct sampling and the addition of one or more chemical compounds (e.g., drugs) as well as the addition of new cells or removal of cells. In these open cartridge embodiments wells 91/bio-reactors 20 can include removable covers 93 that fit over well 91 protecting the bio-reactor and cells from exposure to the air but still allowing the user quick access to the well. Cover 93 can also include ports 94 such as a luer lock or other fitting that allow samples to be withdrawn from the well while the cover is still on.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the bio-reactor circuit can be configured for use in studying a variety of cell types and organ systems including the GI, hepatic, renal and neural and cardiovascular systems. Also they can be used to not only study the effects of various treatments on cells and organ systems but also as in vitro incubators for growing stem cells and other cells for subsequent in vivo use. They can also be configured for both parallel and serial flow or combinations thereof.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method for studying a treatment for a disease or condition on an in vitro level, the method comprising:
   providing a bio-reactor circuit comprising:
      a first bio-reactor having a first chamber including a flow path and a second chamber including cells of a first cell type disposed in the second chamber and a membrane separating the first and second chambers;
      a second bio-reactor having a first chamber including a flow path and a second chamber including cells of a second cell type disposed in the second chamber and a membrane separating the first and second chambers; and
      a pump fluidically coupling the first and second bio-reactors;
   circulating a solution through the circuit;
   providing a treatment for the first cell type in the first bio-reactor;
   analyzing the effect of the treatment on the first cell type in the first bio-reactor; and
   analyzing the effect of the treatment on the second cell type in the second bio-reactor.

2. The method of claim 1, wherein the treatment is provided during a portion of a period when the first cell type is exposed to a compound produced by the second cell type.

3. The method of claim 1, wherein the first cell type is a tumor cell or a cell expressing a gene contributing to a symptom of a disease or condition.

4. The method of claim 3, wherein the expressed gene contributes to under production of a protein, over production of a protein, under production of insulin or production of β-amyloid precursor protein.

5. The method of claim 1, wherein analyzing the effect of the treatment on the first or second cell type comprises measuring a compound secreted by the first or second cell type.

6. The method of claim 1, wherein analyzing the effect of the treatment on the first or second cell type comprises making an optical measurement of the first or second bio-reactor.

7. The method of claim 6, wherein the optical measurement is reflectance, turbidity or fluorescence measurement.

8. The method of claim 6, wherein the optical measurement is made using an array of optical detectors positioned proximate the first or second bio-reactor.

9. The method of claim 6, wherein the optical measurement is used to determine a change in the number of viable cells in the first or second bio-reactor.

10. The bio-reactor circuit of claim 6, wherein the optical measurement is used to determine a change in the expression of a protein by the first or second cell type.

11. The bio-reactor circuit of claim 6, wherein the optical measurement is used to determine a change in the number of bound receptors of the first or second cell type.

12. The method of claim 1, wherein the treatment comprises a thermal treatment or a hypothermic treatment.

13. The method of claim 1, wherein the membrane in at least one of the first or second bio-reactors has a convoluted surface configured to breakdown boundary layers adjacent the membrane so as to enhance diffusion of cell produced compounds and gases through the membrane.

14. The method of claim 1, wherein the cells in at least one of the first or second chambers comprise renal cells.

15. The method of claim 1, wherein the cells in at least one of the first or second chambers comprise adrenal cells.

16. The method of claim 1, wherein the cells in at least one of the first or second chambers comprise pancreatic cells.

17. The method of claim 1, wherein the cells in at least one of the first or second chambers comprise splenic cells.

18. The method of claim 1, wherein the cells in at least one of the first or second chambers comprise hepatic cells.

19. The method of claim 1, wherein the cells in at least one of the first or second chambers comprise myocytes.

20. The method of claim 1, wherein the cells in at least one of the first or second chambers comprise tumor cells.

21. A method for studying a treatment for a disease or condition on an in vitro level, the method comprising:
   providing a bio-reactor circuit comprising:
      a first bio-reactor having a first chamber including a flow path and a second chamber including cells of a first cell type disposed in the second chamber and a membrane separating the first and second chambers;
      a second bio-reactor having a first chamber including a flow path and a second chamber including cells of the first cell type disposed in the second chamber and a membrane separating the first and second chambers; and
      a pump fluidically coupling the first and second bio-reactors;
   circulating a solution through the circuit;
   providing a treatment for the cells in the first bio-reactor, wherein the cells in the second bio-reactor are untreated;
   analyzing the effect of the treatment on the first cell type in the first bio-reactor; and
   comparing the effect of the treatment on cells in the first bio-reactor to cells in the second bio-reactor.

22. The method of claim 21, wherein the membrane in at least one of the first or second bio-reactors has a convoluted surface configured to breakdown boundary layers adjacent the membrane so as to enhance diffusion of cell produced compounds and gases through the membrane.

* * * * *

UNITED STATES PATENT AND TRADEMARK OFFICE
CERTIFICATE OF CORRECTION

PATENT NO. : 10,016,453 B2
APPLICATION NO. : 15/709373
DATED : July 10, 2018
INVENTOR(S) : Mir Imran Page 1 of 1

It is certified that error appears in the above-identified patent and that said Letters Patent is hereby corrected as shown below:

On the Title Page

In Item [56] References Cited:

The eleventh cited U.S. patent document, delete "6,580,563 B1 6/2003 Finney" and replace it with --5,580,563 12/1996 Tam--.

The twelfth cited U.S. patent document, delete "6,635,482 B1 10/2003 Yu et al." and replace it with --5,635,482 6/1997 Bhatnagar--.

In the Claims

Claim 10, Line 1, delete "bio-reactor circuit" and replace it with --method--.

Claim 11, Line 1, delete "bio-reactor circuit" and replace it with --method--.

Signed and Sealed this
Second Day of October, 2018

Andrei Iancu
*Director of the United States Patent and Trademark Office*